US010590463B2

(12) United States Patent
Parissenti et al.

(10) Patent No.: US 10,590,463 B2
(45) Date of Patent: Mar. 17, 2020

(54) DIAGNOSTIC METHODS AND KITS FOR MONITORING RESPONSE TO CHEMOTHERAPY IN OVARIAN CANCER

(75) Inventors: Amadeo Mark Parissenti, Sudbury (CA); Baoqing Guo, Sudbury (CA); Kenneth Pritzker, Toronto (CA); Laura Pritzker, Toronto (CA)

(73) Assignees: RNA Disgnostics Inc., Toronto (CA); Laurentian University of Sudbury, Sudbury (CA)

( * ) Notice: Subject to any disclaimer, the term of this patent is extended or adjusted under 35 U.S.C. 154(b) by 26 days.

(21) Appl. No.: 14/238,132

(22) PCT Filed: Aug. 10, 2011

(86) PCT No.: PCT/CA2011/000907
§ 371 (c)(1),
(2), (4) Date: Apr. 25, 2014

(87) PCT Pub. No.: WO2013/020201
PCT Pub. Date: Feb. 14, 2013

(65) Prior Publication Data
US 2014/0287063 A1    Sep. 25, 2014

(51) Int. Cl.
*C12Q 1/68*         (2018.01)
*C12Q 1/6886*       (2018.01)

(52) U.S. Cl.
CPC ............. *C12Q 1/68* (2013.01); *C12Q 1/6886* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| 6,251,247 B1 | 6/2001 | Mitsuhashi et al. |
| 7,888,035 B2 | 2/2011 | Klass et al. |
| 7,968,291 B2 | 6/2011 | Brees et al. |
| 2011/0177064 A1* | 7/2011 | Whiteman ......... C07K 16/2803 424/133.1 |

FOREIGN PATENT DOCUMENTS

| AU | 2008295394 | 3/2009 |
| EP | 1772522 | 4/2007 |
| JP | 5602018 | 10/2014 |
| WO | 2009030029 | 3/2009 |

OTHER PUBLICATIONS

Enard et al. (Science 2002 vol. 296 p. 340).*
Schroeder et al. (BMC Molecular Biology 2006 vol. 7:3).*
Dermer et al. (Biotechnology vol. 12, Mar. 1994, p. 320).*
Eastham et al. (Int. J. Radiat. Biool. vol. 77, No. 3, pp. 295-302, 2001).*
Ahern (The Scientist Jul. 24, 1995 vol. 9 Issue (Year: 1995).*
Wiklund et al. (Int Journal of Cancer 2010 vol. 126 pp. 28-40) (Year: 2010).*
Wong et al., "Reduced Plasma RNA Integrity in Nasopharyngealcarcinoma Patients", Clinical Cancer Research, Apr. 15, 2006, 12:2512-2516, 12(8).
Parissenti A. M. et al., "Relationship of tumor RNA integrity to clinicopathologic parameters associated with epirubicin/docetaxel chemotherapy", 2007 Breast Cancer Symposium, Sep. 7 and 8, 2007, Abstract No. 107.
Parissenti A. M. et al., "Relationship of tumor RNA integrity to clinicopathologic parameters associated with epirubicin/docetaxel chemotherapy", 2007 Breast Cancer Symposium, Sep. 7 and 8, 2007, (Poster).
Parissenti A. M. et al., "Relationship of tumor RNA integrity to clinicopathologic parameters associated with epirubicin/docetaxel chemotherapy", Nov. 2007, Making Connections: A Canadian Cancer Research Conference Celebrating NCIC's 60th Anniversary, 203-204 (Abstract).
Pandey et al., Induction of the Interferon-Inductible RNA-Degrading Enzyme, RNase L, by Stree-Inducing Agents in the Human Cervical Carcinoma Cells, RNA Biology, May/Jun. 2004, pp. 21-27; 1:1.
Parissenti et al., "Reductions in Tumor RNA Integrity Associated with Clinical Response to Epirubicin/Docetaxel Chemotherapy in Breast Cancer Patients", Cancer Research 69 [Suppl 2], 378s, 2008.
Balatsos et al., "Drug action on poly(A) polymerase activity and isoforms during U937 cell apoptosis", Journal of Experimental and Clinical Cancer Research, Jan. 1, 2001, 20(1):63-69.
Ogston et al., "A new histological grading system to assess response of breast cancers to primary chemotherapy: Prognostic significance and survival", Breast, Oct. 2003, 12(5):320-327.
Carey et al., "Telomerase activity and prognosis in primary breast cancers", Journal of Clinical Oncology, Oct. 1999, 17(10):3075-3081.
Schroeder et al., "The RIN: an RNA integrity number for assigning integrity values to RNA measurements", BMC Molecular Biology, Biomed Central Ltd., Jan. 31, 2006, 7(1):3.
Imbeaud et al., "Towards standardization of RNA quality assessment using user-independent classifiers of microcapillary electrophoresis traces", Nucleic Acids Research, 2005, 33(6):e56, doi:10.1093/nar/gni054.
Wong et al. "Plasma RNA integrity analysis: methodology and validation", Annals of the New York Academy of Sciences, 2006, 1075:174-178.

(Continued)

*Primary Examiner* — Katherine D Salmon
(74) *Attorney, Agent, or Firm* — Bereskin & Parr LLP; Carmela De Luca

(57) ABSTRACT

Provided are methods of determining a response to a chemotherapeutic agent in a subject with ovarian cancer, comprising: determining a RNA integrity value of a sample comprising ovarian cancer cell RNA from the subject after the subject has received one or more doses of the chemotherapeutic agent; wherein a low RNA integrity value and/or RNA degradation of the cancer cell RNA is indicative that the cancer is responding to the chemotherapeutic agent and/or a high RNA integrity value and/or stable RNA integrity of the ovarian cancer cell RNA is indicative that the cancer is resistant to the chemotherapeutic agent.

12 Claims, 4 Drawing Sheets

(56) References Cited

OTHER PUBLICATIONS

Minotti et al., "Anthracyclines: molecular advances and pharmacologic developments in antitumor activity and cardiotoxicity", Pharmacol Rev, 2004, 56:185-229.
Parissenti A. M. et al., "Relationship of tumor RNA integrity to clinicopathologic parameters associated with epirubicin/docetaxel chemotherapy", Internet Citation, Sep. 7, 2007 (Sep. 7, 2007), pp. 1-4.
Strand, Carina et al. RNA quality in frozen breast cancer samples and the influence on gene expression analysis—a comparison of three evaluation methods using microcapillary electrophoreses traces. BMC Molecular Biology 2007, 8:38.
Houge, G., et al. Fine Mapping of 28S rRNA Sites Specifically Cleaved in Cells Undergoing Apoptosis. Molecular and Cellular Biology, Apr. 1995, vol. 15, No. 4, pp. 2051-2062.
Hoat, Trinh X., et al. Specific cleavage of ribosomal RNA and mRNA during victorin-induced apoptotic cell death in oat. The Plant Journal (2006) 46, pp. 922-933.
Marx, Vivien. RNA Quality: Defining the Good, the Bad, & the Ugly. Genomics Proteomics. Retrieved from Internet www.dnaarrays.org/P_GenProMag.pdf May 4, 2005.
King, KL et al. 28S ribosome degradation in lymphoid cell apoptosis: evidence for caspase and Bcl-2 dependent and independent pathways. Cell Death and Differentiation (2000) 7, 994-1001.
Fimognari, Carmela et al. Protective effect of creatine against RNA damage. Mutation Research 670 (2009) 59-67.
Fimognari, Carmela et al. Corrigendum to "Protective effect of creatine against RNA damage". Mutation Research. 670 (2009) 59-67.
Copois, Virginie et al. Impact of RNA degradation on gene expression profiles: Assessment of different methods to reliably determine RNA quality. Journal of Biotechnology 127 (2007) 549-559.
Banerjee et al., "RNase L-independent specific 28S rRNA cleavage in murine coronavirus-infected cells", Journal of Virology, Oct. 2000, pp. 8793-80, 74(19).
Parissenti et al., "Association of low tumor RNA integrity with response to chemotherapy in breast cancer patients", Breast Cancer Research and Treatment. Jan. 2010, pp. 347-356, 119(2), doi: 10.1007/s10549-009-0531-x.
Kemp et al., "p53 induction and apoptosis in response to radio- and chemotherapy in vivo is tumor-type-dependent", Cancer Research, Jan. 1, 2001, pp. 327-332, 61(1).
Kim et al., "The role of apoptosis in cancer cell survival and therapeutic outcome", Cancer Biology & Therapy, Nov. 2006, pp. 1429-1442, 5:11.
Raman et al., "Quality control in microarray assessment of gene expression in human airway epithelium", BMC Genomics, Oct. 24, 2009, 10:493, doi: 10.1186/1471-2164-10-493.
Samali et al., "The ability to cleave 28S ribosomal RNA during apoptosis is a cell-type dependent trait unrelated to DNA fragmentation", Cell Death and Differentiation, May 1997, pp. 289-293, 4(4).
Gjertsen, Bjorn Tore et al. Multiple apoptotic death types triggered through activation of separate pathways by cAMP and inhibitors of protein phosphatases in one (IPC leukemia) cell line. Journal of Cell Science 107, 3363-3677, 1994.
Greenhalgh D.A. et al. Effect of 5-fluorouracil combination therapy on RNA processing in human colonic carcinoma cells. Br. J. Cancer, 1990, vol. 61, pp. 415-419.
Thadani-Mulero, Maria et al. Androgen Receptor on the Move: Boarding the Microtubule Expressway to the Nucleus. Cancer Research, 72(18), pp. 4611-4615, 2012.
Cheang, Maggie C. U., et al. Ki67 Index, HER2 Status, and Prognosis of Patients With Luminal B Breast Cancer. J. Natl. Cancer Institute, 2009, 101, pp. 736-750.
Goldhirsch A. et al. Strategies for subtypes—dealing with the diversity of breast cancer: highlights of the St Gallen International Expert Consensus on the Primary Therapy of Early Breast Cancer 2011. Annals of Oncology, vol. 22, pp. 1736-1747, 2011.
Narendrula, Rashmi. Quantitative and qualitative changes in cellular RNA in response of chemotherapy. Oral presentation, Apr. 4, 2012.
Johnson G.D. et al. "Cleavage of rRNA ensures translational cessation in sperm at fertilization, Molecular Human Reproduction", Aug. 2011, pp. 721-726, 17(12).
Fimognari et al., "RNA as a new target for toxic and protective agents", Mutation Research, Sep. 2008, pp. 15-22, 648(1-2).
Telli M. et al., "Insight or Confusion: Survival After Response-Guided Neoadjuvant Chemotherapy in Breast Cancer", Journal of Clinical Oncology, Oct. 2013 pp. 3613-3615, 31(29).
Young, L.E. Zeroing in on cancer. Laurentian University Magazine, Winter 2010, p. 5. Retrieved from the internet <URL:http://www.laurentian.ca/NR/rdonlyres/D6249D37-F645-49F1-8CA0-1EA940D81CB4/0/Winter10_English_low.pdf>.
Hannemann J. et al. Changes in Gene Expression Associated With Response to Neoadjuvant Chemotherapy in Breast Cancer, Journal of Clinical Oncology, May 2005, 3331-3342, 23(15).
Sotiriou et al. (200) Gene expression profiles derived from fine needle aspiration correlate with response to chemotherapy in breast cancer. Breast Cancer Research. 4:R3 (8 pages).
Thisted. (1998) What is a P-Value? The University of Chicago, p. 1-6.
Fleige et al. (2006) RNA integrity and the effect on the real-time qRT-PCR performance. Molecular Aspects of Medicine, 27:126-139.
Thuerigen et al. (2006). Gene Expression Signature Predicting Pathologic Complete R esponse with Gemcitabine, Epirubicin, and Docetaxel in Primary Breast Cancer, Journal of Clinical Oncology, 24(12):1839-1845.
Degen et al. (2000) Caspase-dependent cleavage of nucleic acids. Cell Death and Differentiation, 7:616-627.
Fulda et al. (2006) Extrinsic versus intrinsic apoptosis pathways in anticancer chemotherapy. Oncogene, 25:4798-4811.
Kaufman et al. (2000) Induction of Apoptosis by Cancer Chemotherapy. Experimental Cell Research, 256:42-49.
Weigelt et al., "Gene expression profiles of primary breast tumors maintained in distant metastases", PNAS, Dec. 23, 2003, 100(26):15901-15905.
Hurvitz et al., "Final Analysis of a Phase II, 3-Arm, Randomized Trial of Neoadjuvant Trastuzumab or Lapatinib or the Combination of Trastuzumab and Lapatinib, Followed by 6 cycles of Docetaxel and Carboplatin with Trastuzumab and/or Lapatinib in Patients with HER2+ Breast Cancer (TRIO-US B07)", San Antonio Breast Cancer Symposium Cancer Therapy and Research Center at UT Health Science Center Dec. 10-14, 2013 (poster).
Neschadim et al. "Relaxin receptor antagonist AT-001synergizes with docetaxel in androgen-independent prostate xenografts" Endocrine-Related Cancer. May 8, 2014;21(3):459-71.
O'Neil VJ et al. A dose-finding stydy of carboplatin—epirubicin—docetaxel in advanced epithelial ovarian cancer. British Journal of Cancer, 2002, vol. 86, pp. 1385-1390.
Samkari, A., et al. Tumor RNA disruption as a tool to predict response to neoadjuvant chemotherapy in breast cancer: Optimizing timing of biopsy. (2016) Abstract No. P1-09-19 [abstract]. In: Proceedings of the 2016 San Antonio Breast Cancer Symposium; Dec. 6-10, 2016; San Antonio, TX. Philadelphia (PA): AACR; Cancer Res 2017; 77 (4 suppl): Abstract, 5 pages (Year: 2017).
Pritzker K., et al. RNA Disruption and Drug Response in Breast Cancer Primary Systemic Therapy. Journal of the National Cancer Institute, 2015, 51:76-80.
He, Kaiyu et al. Targets and Intracellular Signaling Mechanisms for Deoxynivalenol-Induced Ribosomal RNA Cleavage. Toxicological Sciences, 127(2), 382-390, 2012.
Handbook, Qiagen. Sample & Assay Technologies, "RNeasy® MinElute® Cleanup Handbook: For RNA cleanup and concentration with small elution volumes", Oct. 1, 2010, pp. 1-32.

* cited by examiner

DIAGNOSTIC METHODS AND KITS FOR MONITORING RESPONSE TO CHEMOTHERAPY IN OVARIAN CANCER

CROSS-REFERENCE TO RELATED APPLICATIONS

This application is a national phase entry of PCT/CA2011/000907, filed Aug. 10, 2011 which is being incorporated herein in its entirety by reference.

FIELD OF THE DISCLOSURE

The disclosure relates to methods and kits for monitoring response of subjects with ovarian cancer treated to chemotherapy.

INTRODUCTION

PCT application (PCT/CA2008/001561) entitled "Method of Using Tumour RNA Integrity to Measure Response to Chemotherapy in Cancer Patients herein incorporated by reference discloses a method for monitoring response to chemotherapy in patients with locally advanced breast cancer by monitoring the ability of the chemotherapy agents to induce RNA degradation (loss of RNA integrity), as exhibited through a reduction in known metrics of RNA quality, including the RNA integrity number (RIN) [1].

In association with a national clinical trial (CAN-NCIC-CTG-MA.22), it was demonstrated that tumour RIN values fell significantly upon treatment of locally advanced breast cancer patients with epirubicin/docetaxel chemotherapy and this response could be significantly correlated with the dose level of the regimen (p=0.05) [2]. Epirubicin, is an epimer of doxorubicin, and both compounds (known as anthracyclines) intercalate between DNA strands within cells [3]. The drugs also inhibit topoisomerase II [4] and DNA helicase [5], thereby blocking DNA replication. In addition, the drugs are cytotoxic through the generation of free radicals, damaging a variety of macromolecules including DNA and lipids [6]. Docetaxel, in contrast, is an analog of paclitaxel. Both drugs (known as taxanes) bind to microtubules and prevent their depolymerisation [7]. This results in arrest of cell cycle progression at mitosis and mitotic catastrophe [8], and ultimately, the induction of apoptosis [9]. Unlike tumour extent (cellularity) mid-treatment, we observed in the MA.22 clinical trial that low mid-treatment tumour RIN values were predictive of pathologic complete response following treatment in these patients (p=0.05) [2].

SUMMARY

An aspect includes a method of determining responsiveness of an ovarian cancer cell to a chemotherapeutic agent, comprising:
  a. determining a RNA integrity value of a RNA sample of the cancer cell after the cell has been contacted with one or more doses of the chemotherapeutic agent;
wherein a low RNA integrity value is indicative that the cancer cell is responsive to the chemotherapeutic agent and/or a high RNA integrity value is indicative that the cancer cell is resistant to the chemotherapeutic agent.

A further aspect provides a method of determining a response to a chemotherapeutic agent in a subject with ovarian cancer, comprising:
  a. determining a RNA integrity value of a RNA sample comprising ovarian cancer cell RNA from the subject after the subject has received one or more doses of the chemotherapeutic agent and/or one or more cycles of a chemotherapy regimen;
wherein a low RNA integrity value and/or RNA degradation of the cancer cell RNA is indicative that the cancer is responding to the chemotherapeutic agent and/or a high RNA integrity value and/or stable RNA integrity of the cancer cell RNA is indicative that the cancer is resistant to the chemotherapeutic agent.

Yet a further aspect comprises a method of predicting outcome in a subject with ovarian cancer, comprising:
  a. determining a RNA integrity value of a RNA sample comprising ovarian cancer cell RNA from the subject after the subject has received one or more doses of the chemotherapeutic agent and/or one or more cycles of a chemotherapy regimen;
wherein a low RNA integrity and/or RNA degradation of the cancer cell RNA predicts a positive treatment outcome and/or a high RNA integrity and/or a stable RNA quality predicts a negative treatment outcome.

A further aspect includes method of predicting a treatment outcome of a subject having ovarian cancer, the method comprising: determining a RNA integrity value for an ovarian cancer cell RNA sample from the subject, wherein the subject has been treated with one or more doses of a chemotherapeutic agent and/or one or more cycles of a chemotherapy regimen, wherein a RNA integrity value that is below a response threshold predicts an outcome comprising response to the chemotherapeutic agent and a decreased risk of progression; and a RNA integrity value that is higher than the response threshold predicts an outcome comprising cancer resistance to the chemotherapeutic agent and an increased risk of disease progression.

Another aspect includes a method of determining a chemotherapy treatment for a subject with ovarian cancer comprising:
  a. determining cancer responsiveness to a chemotherapeutic agent according to any one of claims 1 to 20; and
  b. continuing the chemotherapy treatment if the RNA integrity of the cancer cell RNA sample is below a response threshold and altering the cancer treatment, for example altering the dosage level and/or changing to an alternate cancer treatment, if the RNA integrity is higher than the response threshold.

In an embodiment, the chemotherapeutic agent is selected from taxanes, anthracyclines, vinca alkaloids such as vinblastine, alkylating agents such as cisplatin and nucleoside analogs such as 5-FU and combinations thereof.

Also provided in another aspect is a kit for use in a method disclosed comprising a RNA isolating composition and an RNAse free vessel for receiving the sample, wherein the vessel is labeled with an identifier permitting for anonymous testing.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment is described in relation to the drawings.

DETAILED DESCRIPTION

Figure 1:
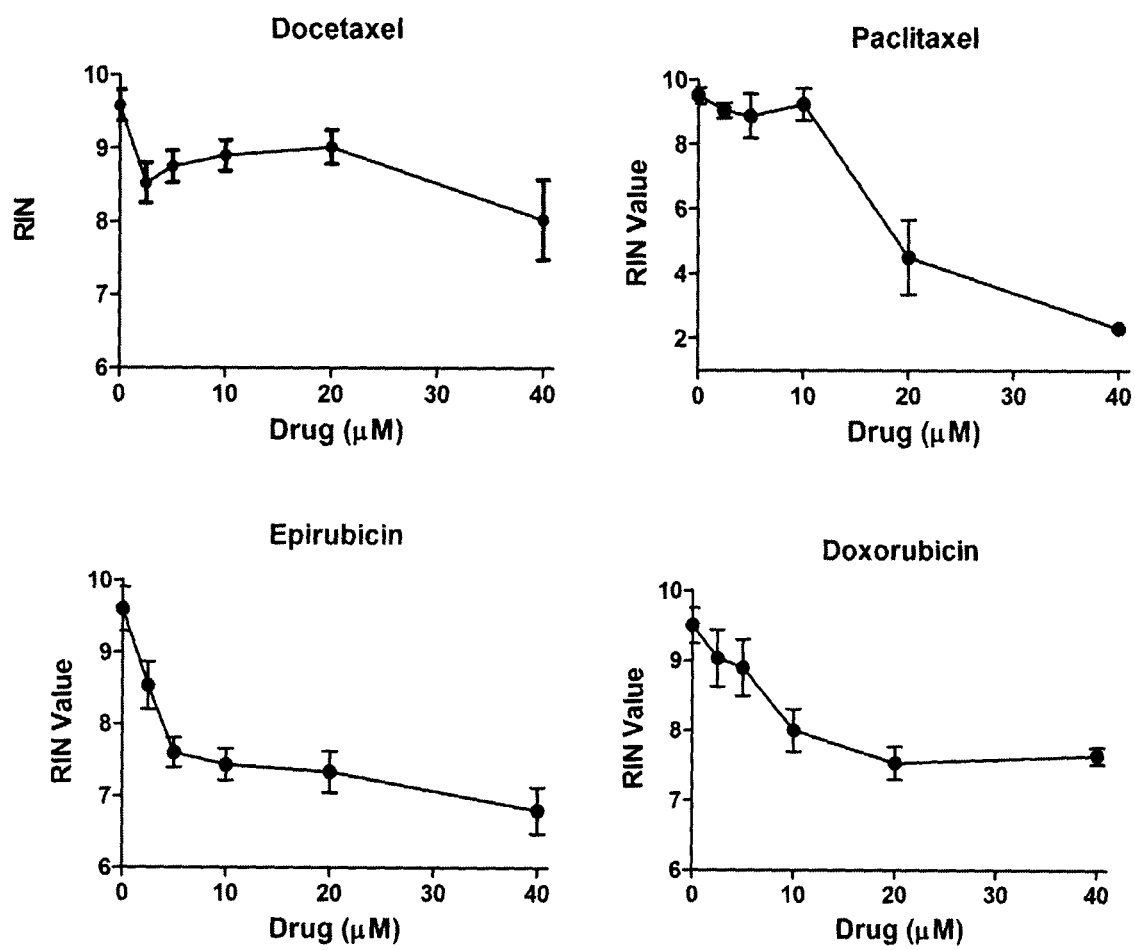
FIG. 1 depicts a series of graphs showing the effects of various anthracyclines and taxanes on RIN.

In the following passages, different aspects of the disclosure are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

I. Definitions

The term "changing cancer treatment" as used herein includes for example one or more of changing the dosage level, discontinuing the agent(s), adding an adjunct chemotherapeutic agent(s) to the chemotherapy treatment or changing to an alternate cancer treatment such as a different drug, surgery or radiation.

The term "comparable to a control" as used herein means a less than 30% decrease, less than 25% decrease, less than 20% decrease from the control such as a pretreatment control, being compared to.

The term "control" as used herein refers to a comparator sample from a subject or a group of individuals who are known as non-responders and/or a reference sample such as a pretreatment sample or earlier sample. For example, the control can be a sample from a subject comprising ovarian cancer cell RNA, such as a pretreatment sample from the subject. The control can also be the expected RNA integrity value for an untreated cancer tissue or cancer cell RNA sample. For example, an untreated cancer tissue or untreated cancer cell RNA sample can be determined and is expected to be "intact", for example have a RIN value of greater than 7, greater than 8, or greater than 9.

The term "chemotherapeutic agent" as used herein means any drug or drug combination used for the treatment of ovarian cancer, including for example drugs used for primary chemotherapy including for example a platinating agent (e.g. cisplatin and/or carboplatin) and/or a taxane (e.g. paclitaxel and/or docetaxel)], or drugs typically used in the treatment of recurrent ovarian cancer (e.g. anthracyclines such as doxorubicin or epirubicin or their pegylated forms), topoisomerase I and II inhibitors (e.g. topotecan and etoposide, respectively), nucleoside analogs such as gemcitabine and 5-fluorouracil, the estrogen receptor blocker tamoxifen, and/or the Her-2/Neu blocker bevacizumab. The chemotherapeutic agent can be administered according to a chemotherapy regimen which comprises administration in cycles. For example, a chemotherapy regimen can comprise 4, 5, 6, 7, or 8 or more cycles.

A "chemotherapy cycle" or "cycle" as used herein refers to a unit of chemotherapy administration, often representing a series of drugs being administered at various dose levels, comprising optionally the interval comprising administration of a dose or set of doses for example, administered once or several times over one or more days, and optionally a rest or recovery interval, which can be for example 1-3 weeks, and which follows the administration of the dose or set of doses. A new cycle occurs with the administration of a subsequent dose or set of doses. Chemotherapy can for example be delivered in multiple cycles for a specific time period.

The term "Chemotherapy dose" or "dose" as used herein refers to doses of individual drug either administered at each time within a schedule OR the total amount of each drug administered within a schedule or the total amount of drug administered during a course of chemotherapy.

The term "decreased RNA integrity" as used herein means an RNA integrity that is at least 20%, at least 25%, at least 30%, at least 40%, at least 50%, at least 60%, at least 70%, at least 80% or at least 90% less than a control for example a pretreatment sample or for example a maximal value (e.g. maximal RIN).

The term "positive treatment outcome" as used herein refers to a positive therapeutic response to treatment, for example alleviation or amelioration of one or more symptoms or conditions, diminishment of extent of disease, stabilized (i.e. not worsening) state of disease, preventing spread of disease or preventing disease progression, delay or slowing of disease progression, reversal of disease, amelioration or palliation of the disease state, and remission (whether partial or total), whether detectable or undetectable. "A positive treatment outcome" can also mean prolonging survival and/or progression free survival as compared to expected survival if not receiving treatment, including for example a pathological complete response post-treatment. The extent of the positive treatment outcome can be for example related to the extent of RNA degradation determined for a cancer sample obtained during treatment.

The term "determining a RNA integrity value" as used herein means performing an assay on a RNA sample for ascertaining or measuring quantitatively or semi-quantitatively the degradation and/or intactness or RNA or a fraction thereof to provide a value representative of the assay results. For example, the RNA integrity value can be determined by a number of methods involving microcapillary electrophoresis, for example by determining a RNA integrity number using for example an Agilent Bioanalyzer machine, an Experion® Capillary Electrophoresis System with its equivalent RNA Quality Index (RQI), Nanodrop® (Thermo Scientific, Inc.) or other equivalent systems, such as those manufactured by Applied Biosystems, Lumex, or Beckman Coulter Corporation or similar system, and/or for example In where the RNA integrity value is a 28S:18s rRNA ratio, determined using gel agarose electrophoresis and/or spectroscopy, for example by assessing UV absorbance at 280:260.

The term "negative treatment outcome" to a lack of a therapeutic response to the treatment, for example recurrence, spread of disease and/or disease progression.

The term "responders" as used here means subjects that demonstrate a positive treatment or therapeutic outcome, including for example, a measurable therapeutic response.

The term "non-responders" as used herein means subjects (e.g. non-responders) that do not demonstrate a positive treatment outcome including for example no measurable therapeutic response, for example exhibit a negative therapeutic outcome.

The term "RNA sample" means any sample comprising purified and/or isolated RNA, including any purified and/or isolated RNA fraction such as total RNA, rRNA, and/or mRNA. In an embodiment, the RNA sample comprises rRNA.

The term "ovarian cancer" as used herein means all subtypes of ovarian cancer, including the serous, clear cell, endometrioid, and mucinous subtypes [10], all of which can be for example treated with the chemotherapy agents described above.

The term "RNA degradation" as used herein means a decrease in the RNA integrity of isolated tumour cell or tissue RNA compared to RNA from untreated cells or tissues. For example, human RNA (e.g. isolated from primary cells and/or tissue) is commonly recognized as degraded when RIN is <7, and/or optionally <7, less than 6.8, less than 6.6, less than 6.4, less than 6.2, less than, 6.0, less than 5.8, less than 5.6, less than 5.4, less than 5.2 or less than 5.0 and for cell lines when RIN is for example =<8.

The term "RNA integrity" as used herein means to the degree of intactness of the RNA following extraction or isolation from the cell or tissue e.g. whether the isolated RNA is degraded. High RNA quality is commonly taken as meaning little to no degradation, for example less than a 30% decrease, less than 25% decrease, less than 20% decrease from maximal RIN, e.g. RIN=10, and/or a control such as a pretreatment control and retention of capacity to amplify mRNAs of interest following extraction or isolation. Low quality RNA is for example RNA that exhibits greater than 20%, greater than 25%, greater than 30%, greater than 35%, greater than 40%, greater than 45%, greater than 50%, greater than 55%, greater than 60%, greater than 65%, greater than 70%, or greater than 75% decrease from maximal RIN, RIN=10 and/or a control such as a pretreatment control or decreased capacity to amplify mRNAs of interest when they are known to be present in controls in RNA following extraction or isolation.

The term "RNA isolating or stabilizing composition" as used herein refers to any composition that inhibits RNAse activity and/or stabilizes RNA preventing RNA degradation.

The term "stable RNA integrity" as used herein means RNA that is not degraded appreciably, for example as compared to an appropriate comparator sample or the expected RNA integrity for the cell type of tissue. Typically for humans this is isolated RNA with RIN=>7, and can be for example in the context of tumour cell RNA=>6.8, =>6.6, =>6.4, =>6.2, =>6.0, or =>5.8 and for cell lines, for example RIN=>9.

The term "RNA integrity value" is a number reflective of the RNA integrity of sample, for example the RNA integrity value can be a spectrophotometer intensity measurement, an RNA integrity number, determined for example using an Agilent Bioanalyzer, and/or a 28S:18S ribosomal RNA ratio.

The term "subject" as used herein refers to any member of the animal kingdom, preferably a human being including for example a subject that has or is suspected of having ovarian cancer.

The term "RNA" as used herein includes any RNA or RNA fraction, including but not limited to total RNA, rRNA and/or mRNA, of subset of RNAs for example RNA can include the total of RNA types and components that may be present following RNA isolation, for example ribosomal RNAs (rRNAs) messenger RNAs (mRNAs), or fractions comprising for example at least rRNA. As an example, total RNA can be used with the methods described herein or a class or subset of RNAs can also be used. For example, RNA subsets that can be assayed with the methods described include for example subsets comprising rRNA, and/or mRNA.

The term "resistant" as used herein refers to an ovarian cancer cell or tumour response to a chemotherapeutic agent or chemotherapy regimen, where the cancer cells or subset of cancer cells within a tumour show no or little response to the chemotherapeutic agent or regimen in terms of RNA degradation, which is associated for example with a negative treatment outcome for the subject having the ovarian tumour.

The term "response" as used herein refers to an ovarian cancer cell or tumor response to a chemotherapeutic agent and/or chemotherapy regimen, where the cancer cells or subset of cancer cells within a tumour respond to the chemotherapeutic agent or regimen in terms of RNA degradation—eg. show significant RNA degradation, which is associated for example with a positive treatment outcome for the subject having the ovarian tumour.

The term "low risk" as used in relation to progression refers to less than average risk (e.g. decreased probability) calculated for a group of patients with the same cancer, treated similarly; and high risk of progression means greater than average risk (e.g. increased probability) compared to the group of patients.

The term "response threshold" as used herein can be a cut-off, above or below which a cancer cell type or tumour is identified as being resistant or responsive to treatment and indicative of patient outcome. For example, a test subject that has a RNA integrity value below a cut-off or response threshold is indicated to be responsive to the chemotherapeutic agent and/or regimen and/or predicts positive treatment outcome.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, reversal of disease, amelioration or palliation of the disease state, and remission (whether partial or total), whether detectable or undetectable. "Treatment" can also mean prolonging survival as compared to expected survival if not receiving treatment.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a," "an," and "the" include plural referents unless the content clearly dictates otherwise.

II. Methods

It is demonstrated herein that the response of ovarian cancer cells to a chemotherapeutic agent can be assessed by determining the RNA integrity of the cancer cells. Similar to breast cancer cells described in PCT/CA2008/001561, herein incorporated by reference, ovarian cancer cells demonstrate reduced RNA integrity when treated with a chemotherapeutic.

Accordingly an aspect of the disclosure includes a method of determining responsiveness of an ovarian cancer cell to a chemotherapeutic agent, comprising:

a. determining a RNA integrity value of a RNA sample of the cancer cell after the cell has been contacted with one or more doses of the chemotherapeutic agent;

wherein a low RNA integrity value is indicative that the cancer cell is responsive to the chemotherapeutic agent and/or a high RNA integrity value is indicative that the cancer cell is resistant to the chemotherapeutic agent:

A low RNA integrity value is reflective of RNA degradation, primarily the degradation of the highly abundant rRNAs. In an embodiment, the RNA sample is total RNA. In another embodiment, the RNA sample is and/or comprises rRNA. In another embodiment, the RNA sample is and/or comprises mRNA.

In an embodiment, the RNA integrity value is a cellular RNA integrity value e.g. a RNA integrity value for cellular RNA.

In an embodiment, the ovarian cancer cell is in vitro. In an embodiment, the ovarian cancer cell is in vivo.

Another embodiment includes a method of determining a response to a chemotherapeutic agent and/or chemotherapy regimen in a subject with ovarian cancer, comprising:

a. determining a RNA integrity value of a RNA sample comprising ovarian cancer cell RNA from the subject after the subject has received one or more doses of a chemotherapeutic agent and/or one or more cycles of a chemotherapy regimen;

wherein a low RNA integrity value and/or RNA degradation of the ovarian cancer cell RNA is indicative that the ovarian cancer is responding to the chemotherapy agent/ and/or regimen and/or a high RNA integrity value and/or stable RNA integrity of the ovarian cancer cell RNA is indicative that the cancer is resistant to the chemotherapeutic agent and/or chemotherapy regimen.

In an embodiment, the response is a therapeutic response e.g. the ovarian cancer response to the chemotherapeutic agent and/or regimen is sufficient to provide a therapeutic benefit to the subject. Therapeutic response is for example predictive of clinical outcome post treatment.

Another aspect includes a method of predicting treatment outcome in a subject with ovarian cancer, comprising:

a. determining a RNA integrity value of a RNA sample comprising ovarian cancer cell RNA from the subject after the subject has received one or more doses of a chemotherapeutic agent and/or cycles of a chemotherapy regimen;

wherein a low RNA integrity and/or RNA degradation of the cancer cell RNA predicts a positive treatment outcome and/or a high RNA integrity and/or a stable RNA quality predicts a negative treatment outcome.

In an embodiment, the positive treatment outcome predicted is pathologic complete response following treatment e.g. extensive RNA degradation of the cancer cell RNA during treatment is predictive of pathologic complete response following treatment. In an embodiment, the positive treatment outcome predicted is reduced risk of disease progression, increased likelihood of disease free survival and/or increased overall survival. In an embodiment, the negative treatment outcome predicted is an increased risk of disease progression, decreased survival and/or recurrence.

The risk of disease progression, length of disease free survival and/or other outcomes are relative to the average or median risk of progression of responders and/or non-responders.

In an embodiment, the method comprises obtaining a RNA sample comprising ovarian cancer cell RNA isolated and/or purified from a tumour sample obtained from the subject after the subject has received one or more doses of a chemotherapeutic agent and/or cycles of the chemotherapy regimen. In an embodiment the method comprises:

a. obtaining a RNA sample comprising ovarian cancer cell RNA isolated and/or purified from an ovarian tumour sample obtained from the subject after the subject has received one or more doses of a chemotherapeutic agent and/or cycles of the chemotherapy regimen; and b. determining the RNA integrity value of the RNA sample.

In an embodiment, the method comprises obtaining an ovarian tumour sample from the subject. In an embodiment, the method comprises:

a. obtaining an ovarian tumour sample from the subject after the subject has received one or more doses of the chemotherapeutic agent and/or chemotherapy regimen; and b. isolating RNA from the ovarian tumour sample to provide a RNA sample comprising ovarian cancer cell RNA; and c. determining the RNA integrity value of the RNA sample comprising ovarian cancer cell RNA.

In an embodiment, the ovarian tumour sample is obtained and/or the RNA sample is from a subject after the subject has received 1, 2, 3, 4 or more doses of the chemotherapeutic agent and/or cycles of the chemotherapy regimen. In an embodiment, the ovarian tumour sample is obtained and/or the RNA sample is from a subject mid-treatment regimen, for example for a 6 week/cycle treatment regimen, the sample is obtained after for example receiving cycle 3. In another embodiment, the ovarian tumour sample is obtained and/or the RNA sample is from a subject post treatment.

The extent or degree of RNA degradation is for example associated with treatment response. Extensive degradation for example can be associated with pathological complete response. A lesser degree of degradation can be associated with lesser than pathological complete response. For example, a subject may not achieve pathological complete but may exhibit some RNA degradation during and/or post-treatment. Such a subject may for example, be treated in a subsequent treatment regimen less aggressively than a subject with no response.

In addition, one or more ovarian tumour and/or RNA samples can be assessed.

In an embodiment, the chemotherapeutic agent is administered in a chemotherapy regimen. In another embodiment, one or more ovarian tumor samples comprising ovarian cancer cell RNA are obtained at one or more times during chemotherapy (after 1, 2, 3, or 4 cycles, and/or any number of cycles or doses) and/or after completion of the chemotherapy regimen. In another embodiment, one or more RNA samples correspond to ovarian tumour samples obtained at one or more times during chemotherapy (after 1, 2, 3, or 4 cycles, and/or any number of cycles or doses) and/or after completion of the chemotherapy regimen.

In an embodiment, the ovarian tumour sample comprises and/or RNA sample is from ovarian cancer cells, for example obtained in cytological or histological biopsy. In an embodiment, the biopsy is divided into two or more ovarian tumour samples and two or more RNA samples are isolated/ purified from the ovarian tumour samples and the RNA integrity value is obtained for each. In an embodiment, an average RNA integrity value of two or more RNA samples is used. In another embodiment, the highest or maximum RNA integrity value of the two or more RNA samples is used.

In an embodiment, the ovarian tumour sample comprises core biopsies, cell scrapes, needle aspirates or fluid comprising tumour cells. For example, for ovarian cancer can comprise peritoneal fluid, specific tumour fine needle aspirates (FNA) and/or core biopsy.

Tumour samples are treated in a manner to minimize RNAse activity, for example, tumour samples are placed immediately in RNA preservative such as RNAlater (Qiagen) or other RNA stabilization reagent or RNA preservative with RNAse inhibitor or flash frozen for example to −80° C., for example using liquid nitrogen. A person skilled in the art would be familiar with the steps taken for obtaining and storing tumour and RNA samples.

In an embodiment, RNA is isolated/purified from the ovarian tumour sample is obtained from the subject prior to determining the RNA integrity value. For example, RNA can be isolated using methods and kits known in the art, including for example Trizol based isolations, column based kits such as total RNA extraction columns and kits. An example of a RNA isolation method is provided in Example 1.

In an embodiment, a low RNA integrity value and/or the level of RNA degradation is relative to a response threshold or control.

Accordingly in embodiments, a RNA integrity value of the ovarian cancer cell RNA that is below a response threshold is indicative the ovarian cancer is responding to the chemotherapeutic agent and/or regimen and/or predicts a positive treatment outcome; and/or a RNA integrity value of the ovarian cancer cell RNA that is higher than a response threshold is indicative the ovarian cancer is resistant to the chemotherapeutic agent and/or regimen and/or predicts a negative treatment outcome.

In an embodiment, the response threshold is a reference or cut-off RNA integrity value from subjects with the same or similar tumour type, for example an ovarian cancer subtype—subjects with a RNA integrity value below or less than the response threshold are predicted (e.g. have an increased probability) to have a positive treatment response.

In another embodiment, the response threshold is a reference or cut-off RNA integrity value from subjects with the same or similar tumour type, for example an ovarian cancer subtype—subjects with a RNA integrity value that is above or higher than the response threshold are predicted to have a negative treatment response.

In another embodiment, the response threshold corresponds to the mean (e.g. average) RNA integrity value for responders and/or non-responders. In an embodiment, the mean RNA integrity value comprises an average of the mean RNA integrity in ovarian cancer cell samples from ovarian cancer subjects that respond to treatment with a chemotherapeutic and/or the mean RNA integrity in ovarian cancer cell samples from ovarian cancer subjects that do not respond to treatment with the chemotherapeutic in another embodiment the response threshold corresponds to a threshold of high negative or positive predictive value or high area under the curve by receiver operator curve analysis or other probability analysis methods. In another embodiment, the response threshold is selected from a mean maximum RNA integrity, median maximum RNA integrity, mean RNA integrity, median RNA integrity, mean minimum RNA integrity, and median minimum RNA integrity of responders and/or non-responders.

The response threshold can comprise for example one or more values. For example a RNA integrity value below a RNA integrity response threshold i), can be indicative of cancer responsiveness and/or positive treatment outcome and a RNA integrity value higher than a response threshold ii), can be indicative of resistance or poor response to the chemotherapeutic agent and/or chemotherapy regimen and/or predicts a negative treatment outcome. For example, there can be a zone between response threshold i) and response threshold ii) that is indeterminate (e.g. indeterminate, for example with respect to predicting treatment outcome. In an embodiment, the response threshold is positive response threshold, below which subjects are predicted to have a positive treatment outcome. In an embodiment, the response threshold is a negative response threshold, above which subjects are predicted to have a negative treatment outcome. In another embodiment, RNA integrity values falling within an indeterminate zone, for example greater than a positive response threshold and less than a negative response threshold, are predicted to have an indeterminate outcome.

In another embodiment the response threshold corresponds to a threshold of high negative or positive predictive value or high area under the curve by receiver operator curve analysis or other probability analysis methods. For example, RNA integrity values can be stratified into multiple zones such as three zones, for example Zone 1: non-responders, high negative predictive value, Zone 2: intermediate to include partial responders (some drug effect but insufficient to achieve response; this zone may include for example up to 15% of responders), and Zone 3: which is selected to include for example 85% of responders, high positive predictive value.

Alternatively, the comparison can be relative to a single response threshold for example a RNA integrity value can be compared to a median or mean RNA integrity value for responders and non-responders wherein a RNA integrity value below a median or mean response of responders and non-responders is indicative of cancer response to the chemotherapeutic agent and/or chemotherapy regimen and/or positive treatment outcome and a RNA integrity value higher than a median or mean RNA integrity value for responders and non-responders is indicative of resistance and/or negative treatment outcome.

In an embodiment, a RNA integrity value below a RNA integrity threshold is indicative of responsiveness and/or good outcome. In an embodiment, the RNA integrity threshold corresponds to a reference value of RNA integrity value for responders and a reference value of RNA integrity value for non-responders.

In an embodiment, a RNA integrity value of the cancer cell RNA that is below or less than a control is indicative the cancer is responding to the chemotherapeutic agent and/or chemotherapy regimen; and/or a RNA integrity value of the cancer cell RNA that is above or higher than a control is indicative the cancer is resistant to the chemotherapeutic agent and/or chemotherapy regimen.

In an embodiment, the control corresponds to a pretreatment RNA integrity value. For example, the control can correspond to the RNA integrity value of a biopsy RNA sample taken from the subject or two or more subjects prior to initiating therapy or reference values from tumours of similar patients prior to therapy. A decrease in RNA integrity compared to the pretreatment RNA integrity value for example, would indicate treatment response and/or positive treatment outcome and for example a comparable RNA integrity value of the cancer cell RNA to the pretreatment RNA integrity value, would indicate resistance negative treatment outcome.

In an embodiment, the RNA integrity value is compared to a control for example, by one or more probability analysis methods. For example, the control can be a subject control, such as a pretreatment sample from the subject. In an embodiment, where the control is a pretreatment subject control, a decrease in the RNA integrity value compared to the pretreatment subject control is indicative or cancer responsiveness and/or positive treatment outcome. In another embodiment, where the control is a pretreatment subject control, a comparable RNA integrity value—and/or stable RNA integrity value—compared to the pretreatment subject control is indicative of cancer resistance to the chemotherapeutic agent and/or chemotherapy regimen and/or negative treatment outcome post treatment. The control can be a population pretreatment control, for example an average, minimum, or maximum RNA integrity value or reference range for two or more subjects with ovarian cancer prior to treatment. In an embodiment, a high RNA integrity value and/or stable RNA integrity is reflected in a comparable RNA integrity compared to a control such as a pre-treatment control or specific external reference standards for RNA degradation.

Another aspect includes a method of predicting a therapeutic outcome for a subject having ovarian cancer, the method comprising: determining a RNA integrity value for an ovarian cancer cell RNA sample from the subject, wherein the subject has been treated with one or more doses of a chemotherapeutic agent and/or cycles of a chemotherapy regimen, wherein a RNA integrity value that is below a response threshold predicts an outcome comprising response to the chemotherapeutic and/or positive treatment outcome such as a decreased risk of progression; and a RNA integrity value that is higher than the response threshold predicts a negative treatment outcome such as an outcome comprising cancer resistance to the chemotherapeutic agent and/or chemotherapy regimen and an increased risk or progression.

Another aspect includes a method of predicting a therapeutic outcome for a subject having ovarian cancer, the method comprising: determining a RNA integrity value for an ovarian cancer cell RNA sample from the subject, wherein the subject has been treated with one or more doses of a chemotherapeutic agent and/or cycles chemotherapy regimen, wherein a RNA integrity value that comparable to a control and/or stable RNA integrity predicts a negative treatment outcome such as an outcome comprising cancer resistance to the chemotherapeutic agent and/or chemotherapy regimen and an increased risk or progression.

Ovarian cancer cells that do not exhibit significant RNA degradation (e.g. exhibit stable RNA integrity and/or comprises a RNA integrity value comparable to a control such as a pretreatment value) are predicted for example to be resistant to the chemotherapeutic agent and/or chemotherapy regimen. For example, where the control is a subject pretreatment control or population of pretreatment control, comparable RNA integrity values include for example less than 30%, less than 25%, less than 20%, or less than 15% difference from the control.

A further aspect includes a method to predict an expected lack of response to chemotherapeutic agent in a subject having ovarian cancer, comprising determining a RNA integrity value of a RNA sample of ovarian cancer cell RNA from the subject for a RNA integrity value that is higher than the response threshold and/or comparable to a control, for example the mean RNA integrity value in ovarian cancer cells; wherein the mean response threshold is determined from the mean RNA integrity values in cancer cell RNA samples from cancer subjects that respond to treatment with the chemotherapeutic agent and/or cancer subjects that do not respond to treatment with the chemotherapeutic agent.

Yet a further aspect includes a method of determining a subject's responsiveness to a chemotherapeutic agent, in a subject with an ovarian cancer comprising determining a RNA integrity value of ovarian cancer cells obtained from the subject before administration of the chemotherapeutic agent (e.g. control cells), and comparing to the RNA integrity value of cancer cells determined after administration of one or more doses of a chemotherapeutic agent and/or one or more cycles of a chemotherapy regimen, wherein a decrease in the RNA integrity value after administration of the chemotherapeutic agent indicates that the subject is responsive to the chemotherapeutic agent.

In an embodiment, the RNA integrity value is below a RNA integrity of a prior tumour and/or RNA sample (e.g. control sample) comprising ovarian cancer cell RNA obtained from the subject prior to obtaining the sample, for example in step (a), preferably wherein the prior sample comprises a RNA sample from the subject prior to the subject receiving the one or more doses of the chemotherapeutic agent and/or one or more cycles of a chemotherapy regimen, for example a pretreatment sample.

In an embodiment, the RNA integrity value indicative of responsiveness and/or positive treatment outcome is decreased at least by 20%, at least 25%, at least 30%, at least 35%, at least 40%, at least 50%, at least 60%, at least 70%, at least 80% or at least 90% below a control such as a pretreatment sample.

In an embodiment, the RNA integrity value indicative of resistance (e.g. or non-responders) and/or negative treatment outcome is decreased less than 40%, less than 35%, less than 30%, less than 25%, less than 20%, or less than 10% or is increased or comparable compared to a control.

The RNA integrity value can be determined for example by any method that assesses the state of RNA degradation in cancer cell RNA.

In an embodiment, the RNA assessed is denatured. In an embodiment, the RNA assessed is non-denatured.

In an embodiment, the RNA integrity value is determined by calculating a RNA integrity number (RIN) for example using a method that involves using microfluidics, microcapillary electrophoresis, and fluorescent dyes, for example using an Agilent Bioanalyzer machine, an Experion® Capillary Electrophoresis System with its equivalent RNA Quality Index (RQI), Nanodrop® (Thermo Scientific, Inc.) or other equivalent systems, such as those manufactured by Applied Biosystems, Lumex, or Beckman Coulter Corporation or similar system. In an embodiment, the method comprises separating the RNA by electrophoresis, detecting RNA for example with fluorescent dye and quantitating RNA integrity.

Recently, microcapillary electrophoresis has been used increasingly to assess RNA integrity, particularly since only nanogram quantities of RNA are required. One such platform, the Agilent® 2100 Bioanalyzer (Agilent Technologies, Inc., U.S.A.) uses microfluidics technology to carry out electrophoretic separations of RNAs in an automated, reproducible manner (Mueller, O. et al., *Electrophoresis* 21 (2000) 128-134). The Agilent® 2100 Bioanalyzer is now used in many laboratories for the assessment of RNA quality. The development of software for the Agilent®

Bioanalyzer allows calculation of an RNA integrity number (RIN) for each sample after capillary electrophoresis. (Schroeder, A. et al., *BMC. Mol. Biol.* 7 (2006) 3; Imbeaud, S. et al. *Nucl. Acids Res.* (2005), 33, 6, e56, 1-12). This software incorporates an algorithm which quantifies the amounts of multiple RNAs in the electropherogram of a given RNA sample and assigns a RIN value based on this assessment.

For example the Agilent Bioanalyzer uses fluorescent dyes that bind to nucleic acid to evaluate RNA concentration and integrity. RNA moves through a separation channel of a RNA chip, and intercalating dye binds the RNA. The fluorescence of these molecules is measured as they pass a detector.

In an embodiment, between 20-250 ng of RNA is assessed or any number in between. In another embodiment, about 0.5 ng about 1 ng, about 5 ng, about 10 ng, about 20 ng, about 30 ng, about 40 ng, about 50 ng is assessed. In another embodiment.

In an embodiment, the RNA integrity value is expressed as an RNA integrity number (RIN), wherein the RIN comprises a calculation of RNA integrity of multiple RNAs, preferably wherein the RIN is calculated using one or more of a RIN algorithm, an analytic electrophoresis system, or a RNA chip.

In an embodiment, a RIN indicative of cancer responsiveness and/or positive treatment outcome is less than 4.5, less than 3.5, less than 3, less than 2.5, less than 2, less than 1.5 and/or less than 1. Accordingly in an embodiment the response threshold is about 4.5, about 4.0, about 3.9, about 3.8, about 3.7, about 3.6, about 3.5, about 3, about 2.5, about 2, about 1.5 or about 1 and a cancer cell RIN below the response threshold is indicative of response and/or positive treatment outcome.

In an embodiment, a RIN indicative of cancer resistance and/or negative treatment outcome is greater than 5, greater than 5.5, greater than 6, greater than 6.1, greater than 6.2, greater than 6.3, greater than 6.4, greater than 6.5, greater than 7, greater than 7.5 or greater than 8 and a cancer cell RIN higher than a response threshold of about 5, about 5.5, about 6, about 6.1, about 6.2, about 6.3, about 6.4, about 6.5, about 7, about 7.5 or about 8 is indicative of resistance and/or negative treatment outcome.

In an embodiment, the RNA integrity is determined by calculating a 28S:18S ribosomal (rRNA) ratio (e.g. 28S/18S rRNA ratio).

A 28S rRNA:18S rRNA ratio can be determined for example by using for example denaturing agarose gel systems which can include for example either formaldehyde and MOPs buffer, or glyoxal in the loading buffer, to denature the RNA allowing molecules to run by size. The 28S and 18S rRNA bands can be visualized for example by ethidium bromide staining or other more sensitive dyes such as RiboGreen®.

For example, RNA integrity can be evaluated by visualization of RNA bands under ultraviolet light after gel electrophoresis and staining of the gel with ethidium bromide. Typically, the intensity values for the 28S and 18S rRNA bands are determined by film densitometry and a 28S/18S rRNA ratio computed. RNA is considered of high quality if the 28S/18S rRNA ratio is about 2.0 or higher.

In an embodiment, the RNA integrity value and/or the 28S:18s rRNA ratio is determined using spectroscopy, for example by assessing UV absorbance at 280:260. In an embodiment the RNA integrity value is a ratio of 28S rRNA and 18S rRNA.

In a further embodiment, the RNA integrity value is determined by assessing the RNA integrity of a subset of RNAs or fraction of total RNA. In an embodiment, the RNA is total RNA, ribosomal RNA or mRNA.

In an embodiment, a mid-treatment RNA integrity value is assessed and/or compared to a response threshold or control. In another embodiment, a post treatment RNA integrity value is assessed and/or compared to response threshold or control.

In an embodiment, the chemotherapeutic agent is selected from one or more of anthracyclines, taxanes and combinations thereof, preferably wherein the chemotherapeutic agent comprises epirubicin, docetaxel or combinations thereof.

In another embodiment, the chemotherapeutic agent is selected from taxanes, anthracyclines, vinca alkaloids such as vinblastine, alkylating agents such as cisplatin and nucleoside analogs such as 5-FU and combinations thereof.

In an embodiment, the taxane is selected from paclitaxel and/or docetaxel and/or combinations thereof.

In another embodiment, the anthracycline is selected from doxorubicin and epirubicin and combinations thereof.

In an embodiment, the chemotherapy agent is selected from epirubicin and docetaxel and combinations thereof.

In an embodiment, the chemotherapy agent is selected from a taxane and epirubicin and combinations thereof.

In another embodiment, the chemotherapeutic agent is paclitaxel.

In an embodiment, the chemotherapeutic agent in any of the methods described herein comprises paclitaxel.

In an embodiment, the method is applied wherein the subject has ovarian cancer and the chemotherapeutic agent being administered is selected from taxanes, anthracyclines, vinca alkaloids such as vinblastine, alkylating agents such as cisplatin and nucleoside analogs such as 5-FU and combinations thereof.

In an embodiment, the chemotherapy regimen comprises one or more chemotherapeutic agents.

In an embodiment, the chemotherapeutic agent comprises a two or more chemotherapeutics for example epirubicin and docetaxel.

The methods described herein permit for example tailoring of chemotherapeutic therapy for subjects with ovarian cancer.

Accordingly a further aspect includes a method of tailoring a chemotherapy treatment in a subject with ovarian cancer comprising:
a. determining cancer responsiveness to a chemotherapeutic agent and/or chemotherapy regimen according to a method described herein; and
b. continuing the chemotherapy treatment if the RNA integrity of the ovarian cancer cell RNA sample is below a response threshold and altering the cancer treatment, for example altering the dosage level and/or changing the chemotherapy agent, if the RNA integrity is higher than the response threshold.

This approach to monitoring chemotherapy response is expected for example to permit non-responding patients (e.g. identified as having moderate to high RNA integrity mid-treatment) to be switched to other treatments (surgery, radiation therapy, or other drugs) without completing the remaining cycles of the ineffective regimen. This may spare patients the toxic side effects of regimens to which their cancers are not responding.

The methods described herein can for example be used to assess and/or stratify subjects in a clinical trial.

A further aspect comprises a method comprising sending an ovarian tumour or RNA sample comprising ovarian cancer cell RNA to a testing site, wherein the sample is for example packaged in a RNAse free vessel and optionally resuspended in a lysis buffer, RNA isolation and/or stabilization composition optionally comprising RNAse inhibitors, the vessel labeled with an identifier permitting, for example, anonymous testing; and receiving from the testing site an assessment of the sample's RNA integrity, including a score or other indicator indicating the risk of treatment failure. The risk assessment can be provided for example to a medical practitioner, who will use the risk assessment based on RNA quality data (in addition to other data) to decide on the best treatment option to recommend to his or her patient.

In an embodiment, the predicted prognosis is positive treatment outcome, negative treatment outcome or indeterminate. In an embodiment, the predicted prognosis is reflected in a numerical scale, for example 1 for positive treatment outcome, 2 for negative treatment outcome and 3 for indeterminate outcome. Other scales and/or formats for risk assessment based on RNA integrity data could be used, as would be understood by a person skilled in the art.

III. Kits

A further aspect includes a kit for practicing a method disclosed herein. In an embodiment, the kit comprises one or more necessary tools for biopsy collection (e.g. syringes for core biopsy collection or the obtainment of fine needle aspirates), a RNA preservative or isolation/stabilization composition optimized for preserving total RNA, mRNA and/or rRNA integrity, and a RNAse free vessel for receiving the tumour and/or RNA sample, wherein the vessel is labeled for example with an identifier permitting for anonymous testing. For example, the vessel is sufficiently rigid for transport on dry ice to a testing site.

In an embodiment, the kit includes one or more of sealable tubes containing an RNA stabilization solution, for example containing a volume that ensures for example the tumour sample is submerged in RNA stabilization solution. In an embodiment, the kit includes a container to securely store the ovarian tumour samples for transfer to our RNA assessment centre. In a further embodiment, the kit includes a syringe for sample acquisition, for example for obtainment of a core biopsy or a fine needle aspirate. The kit can also include for example, a microscope slide and appropriate solutions for obtainment of fixed touch prep.

In an embodiment, the kit comprises instructions and solutions for isolating substantially pure RNA optimized for example for retention of total RNA or rRNA integrity and for determining RNA integrity according to a method described herein.

The following non-limiting examples are illustrative of the present disclosure:

EXAMPLES

Example 1 it is demonstrated herein that the epirubicin/docetaxel combination can induce reductions in RNA integrity in cultured ovarian carcinoma cells, suggesting that the regimen is able to induce RNA degradation (promote loss of RNA integrity) in tumour cell types other than breast. It is also shown that another taxane (paclitaxel) can induce strong reductions in RNA integrity across tumour cell lines originating from a variety of tissue types. Finally, it is shown that a variety of chemotherapy drugs (alone or in combination) can induce reductions in tumour RNA integrity in ovarian carcinoma cells, suggesting that the observed reductions in RNA integrity both in patient tumours and in vitro are not limited to the epirubicin/docetaxel combination or specifically to taxanes and anthracyclines.

Materials and Methods a) Establishment of an In Vitro System to Monitor RNA Degradation in Cultured Tumour Cells:

The serous ovarian cancer cell line A2780 has been found to reproducibly exhibit changes in RNA quality upon exposure to chemotherapy. These cells have thus become part of a useful in vitro assay for studying chemotherapy-dependent RNA degradation. In this assay, A2780 cells are grown in RPMI-1640 medium (w/L-Glutamine, no Hepes, Cat # SH30027.FS, Hyclone) containing 10% fetal bovine serum (FBS) (Cat # SH30396-03, Hyclone), and incubated at 37° C. in a humidified 5% $CO_2$ atmosphere. Unless otherwise stated, $5\times10^5$ cells are introduced into each well of a 6-well tissue culture plate and allowed to adhere overnight, following which the cells are treated for 24 hours with specific chemotherapy drugs. Specifically, cells are placed in: 100% medium, 0% PBS; 50% medium, 50% PBS; 10% medium, 90% PBS, 5% medium, 95% PBS; 2.5% medium, 97.5% PBS, or 0% medium, 100% PBS) for 24 h. In addition, the cells are incubated with or without various molar concentrations of chemotherapy agents (0 µM, 2.5 µM, 5 µM, 10 µM, 20 µM, and 40 µM). In some instances, two chemotherapy drugs are administered together and their effect on RNA quality assessed. Also, in some instances, the time course of RNA degradation induced by chemotherapy drugs is assessed, specifically at 0, 1, 2, 4, 8 and 24 h without the addition of chemotherapy drugs. Such treatments often induce significant detachment of cells from their flasks. Consequently, both floating and adherent cells are collected after the various treatments. Specifically, the cell culture medium (containing the floating cells) is removed from the plate by pipetting and transferred to a 15 mL tube. Adherent cells are then washed with PBS, released from their wells using a cell scraper, and added to the media containing floating cells. The floating and adherent cells are then harvested by centrifugation at 1000 rpm for 5 min. The supernatant is then removed and RNA is isolated from the pelleted cells using either RNeasy (Cat #74106) or miRNeasy (cat #217004) Mini kits from Qiagen Laboratories (Toronto, ON), following the manufacturer's protocols, as described below.

b) Isolation of RNA from Cultured Tumour Cells Chemotherapy Drug Administration:

Materials and Reagents

Qiagen RNAeasy Mini kit (Cat #74106)

Qiagen miRNeasy Mini Kit (Cat #217004)

i) RNeasy Mini Kits:

Before starting RNA isolation, an appropriate volume of buffer RLT is prepared by adding β-mercaptoethanol to buffer RLT in a ratio of 10 µl for every 1 ml of solution. RLT buffer is stable for a month after addition of β-ME. RLT buffer in some instances formed a precipitate upon storage. This precipitate was redissolved by warming at 30° C. and then placing the solution at room temperature. Aliquots of 0.5 ml RLT buffer (with β-ME) were placed in Eppendorf microfuge tubes prior to RNA isolation procedures. After the desired treatments and collection of both floating and adherent cells (as described above), cell are resuspended in 350 µL RLT buffer containing beta-mercaptoethanol. The resulting lysate is passed at least 5 times through a 20-gauge needle (0.9 mm diameter) fitted to an RNase-free syringe to shear associated genomic DNA. The sheared lysate is then transferred to a microcentrifuge tube and centrifuged at maximum speed for 3 minutes, with transfer of the supernatant to a new tube. One volume of 70% ethanol (500 μl) is added to the homogenized lysate, and the sample mixed well by pipetting. If some volume of the lysate is lost during homogenization, the volume of ethanol is adjusted accordingly. Visible precipitates form in some instances after the addition of ethanol, but this appears not to affect the RNA isolation procedure. Up to 700 μl of the sample is then applied to an RNeasy mini column placed in a 2 ml collection tube, including any precipitate that may have formed. The loaded column is subsequently centrifuged for 30 seconds at ≥8000×g (≥10,000 rpm), discarding the flow-through. Any remaining lysate is applied to the column and the column centrifuged as described above, discarding the flow-through. Buffer RW1 (700 μl) is then added to the RNeasy column in a 2 ml microfuge tube to wash the column free of unbound lysate components. The sample is then centrifuged for 30 seconds at ≥8000×g (≥10,000 rpm), discarding the flow-through. The RNeasy column is placed into a new 2 ml microfuge tube and 500 μl of RPE buffer is added to wash the column. After centrifugation for 30 seconds at ≥8000×g (≥10,000 rpm) to remove the wash buffer, two identical washes of the column in RPE buffer are performed. This buffer is supplied as a concentrate, and must be diluted with 4 volumes of ethanol (100%) prior to use. Any residual liquid associated with the column is then removed by centrifugation at full speed for 1 minute. The column is transferred to a 1.5 ml collection tube, after which 35 μl of RNase-free water is applied to the column. After leaving the column at room temperature for 1 minute, the column is centrifuged for 1 min at full speed to collect the eluted RNA. To obtain a higher concentration and complete elution of the RNA from column, a second elution step was performed by reapplying the eluate to the column and centrifuging a second time. A 5 μl aliquot of the eluted RNA sample is reserved for RNA quality assessments (see below), while the remainder of the sample is immediately stored at −80° C. for future use.

ii) miRNeasy Kits:

After the desired treatments and collection of both floating and adherent cells (as described above), the cells are resuspended in 700 μl of QIAzol Lysis Reagent. The cells are homogenized by vortexing for 1 min, after which the homogenate is allowed to incubate at room temperature (15-25° C.) for 5 min. Chloroform (140 μl) is then added to the homogenate and the tube vortexed vigorously for 15 s. After a further incubation at room temperate for 2-3 min, the homogenate is centrifuged for 15 min at 12,000×g at 4° C. The sample after centrifugation contains an upper, colorless, aqueous phase containing RNA, a white interphase, and a lower, red, organic phase. The aqueous phase (typically about 350 μl) is placed in a new collection tube, after which 1.5 volumes (525 μl) of 100% ethanol is added (with thorough mixing by pipetting the sample up and down several times. Up to 700 μl of the sample, including any precipitate that may have formed, is then loaded onto an RNeasy Mini spin column in a 2 ml collection tube. After closing the lid of the spin column, the column is centrifuged at ≥8000×g (~10,000 rpm) for 15 s at room temperature (15-25° C.), discarding of the flow-through. The above step is repeated until the remainder of the sample is loaded onto the column. The column is then washed with the addition of 700 μl of buffer RWT to the column. The wash buffer was removed from the column by centrifugation for 15 s at ≥8000×g (≥10,000 rpm), discarding the flow-through. Two washes of the column with 500 μl of RPE buffer then take place, with removal of the wash buffer by centrifugation at ≥8000×g (≥10,000 rpm) for 15 seconds and 1 minute for the first and second washes, respectively. The washed RNeasy Mini spin column is then transferred to a new 1.5 ml collection tube, after which 35 μl of RNase-free water is added to the RNeasy Mini spin column to elute the RNA from the column. The eluted RNA is harvested from the column by centrifugation for 1 min at ≥8000×g (≥10,000 rpm). To obtain a higher total RNA concentration, a second elution step is performed by reapplying the eluate to the column and repeating the centrifugation step. A 5 μl aliquot of the eluted RNA sample is reserved for RNA quality assessments (see below), while the remainder of the sample is immediately stored at −80° C. for future use.

c) Assessment of RNA Quality and Concentration Using an Agilent 2100 BioAnalyzer with Agilent RNA 6000 Nano Kits and Caliper Technology's RNA Nanochips:

The procedure used for assessing the quantity and quality of the above RNA preparations involved capillary electrophersis on an Agilent 2100 Bioanalyzer (Agilent Technologies, Mississauga, ON) using a protocol described in detail in the Agilent RNA 6000 Nano Kit Guide available at the following url:http://www.genomics.agilent.com/GenericB.aspx?PageType=Product&SubPageType=Product Literature&PageID=1649

This document includes a detailed description on setting up the assay equipment, preparing and running the RNA Nanochips, and analysis of the capillary electrophoretic data using the Agilent 21000 Bioanalyzer and its associated "Expert software". It is important that all "Essential Measurement Practices" described in the document are followed. RNA 6000 "Nanochips" and associated solutions are obtained in RNA 6000 Nano kits that can be purchased from Agilent Technologies (Mississauga, ON). RNA Nanochips are manufactured by Caliper Life Sciences (Hopkinton, Mass.). The sizes of the rRNAs, and the concentration of RNA in a given sample are determined by extrapolation from a standard curve of reference RNAs provided in the RNA 6000 NANO kits. All data from the Bioanalyzer runs were stored both as PDF and XAD files. The Agilent 2100 Expert software was used to obtain all data from the capillary electrophoresis runs, including the RNA quality and quantity for a given RNA preparation.

Results a) Effects of Various Anthracyclines and Taxanes to Induce Reductions in RNA Integrity in A2780 Cells:

Using the above-described methods for treatment of A2780 cells with specific chemotherapy agents, for isolation of RNA (Qiagen miRNeasy from treated and untreated cells, for monitoring RNA integrity in these cells, we were able to assess the ability of two taxanes (paclitaxel and docetaxel) and two anthracyclines (doxorubicin and epirubicin) to induce changes in RNA quality. As shown in this experiment (FIG. 1), docetaxel induced modest reductions in RNA integrity, with little change in RNA integrity at low micromolar concentrations, increasing to a 18.8% reduction at 40 μM docetaxel. In contrast, despite its similar structure, paclitaxel induced highly substantial, dose-dependent reductions in RNA integrity (for example, 52.5% and 75.8% reductions at 20 and 40 μM paclitaxel, respectively). Epirubicin induced substantial dose-dependent reductions in RNA quality (up to 29.2%). Doxorubicin, which is highly similar in structure to epirubicin, also induced substantial reductions in RNA integrity, up to 20.0% at the 40 μM concentration.

Figure 2:
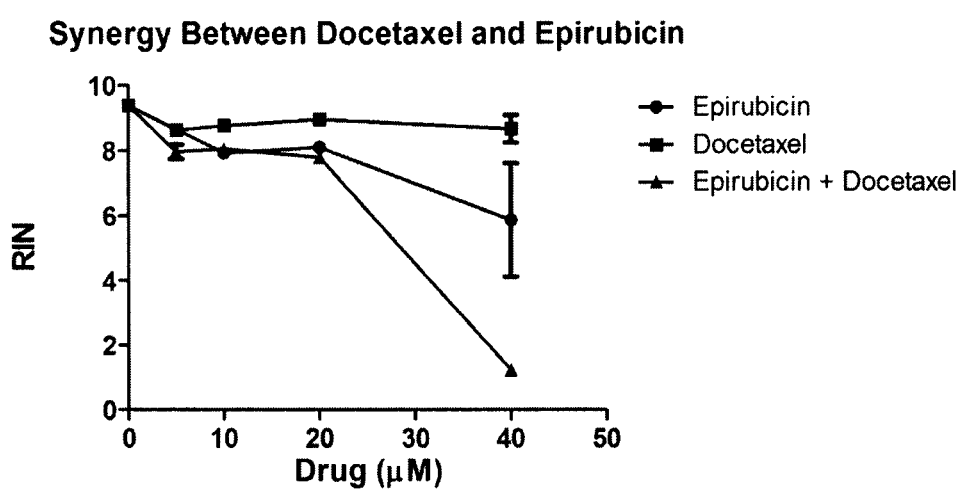
FIG. 2 is a graph showing synergy between Docetaxel and Epirubicin.
Figure 3:
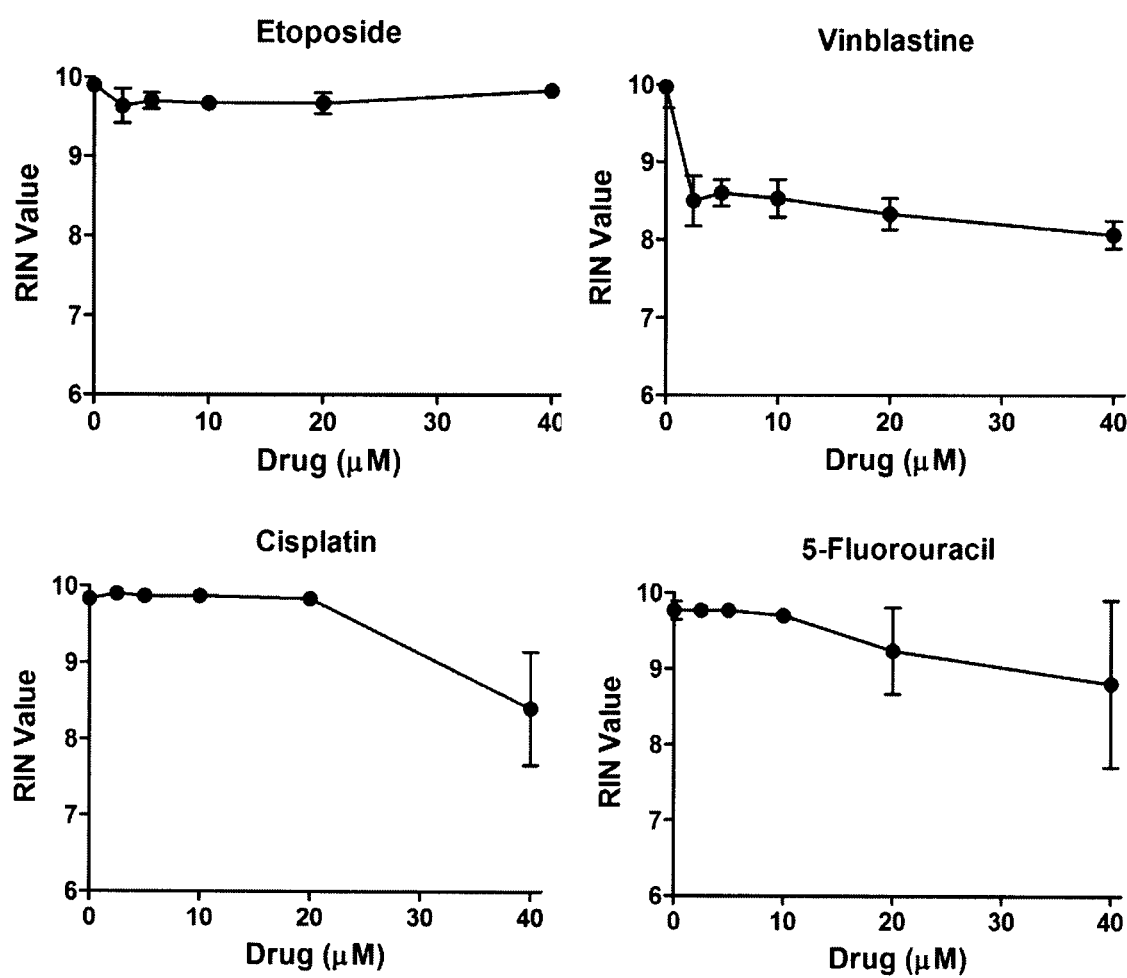
FIG. 3 are graphs showing the effect of different chemotherapeutic agents on RIN.
Figure 4:
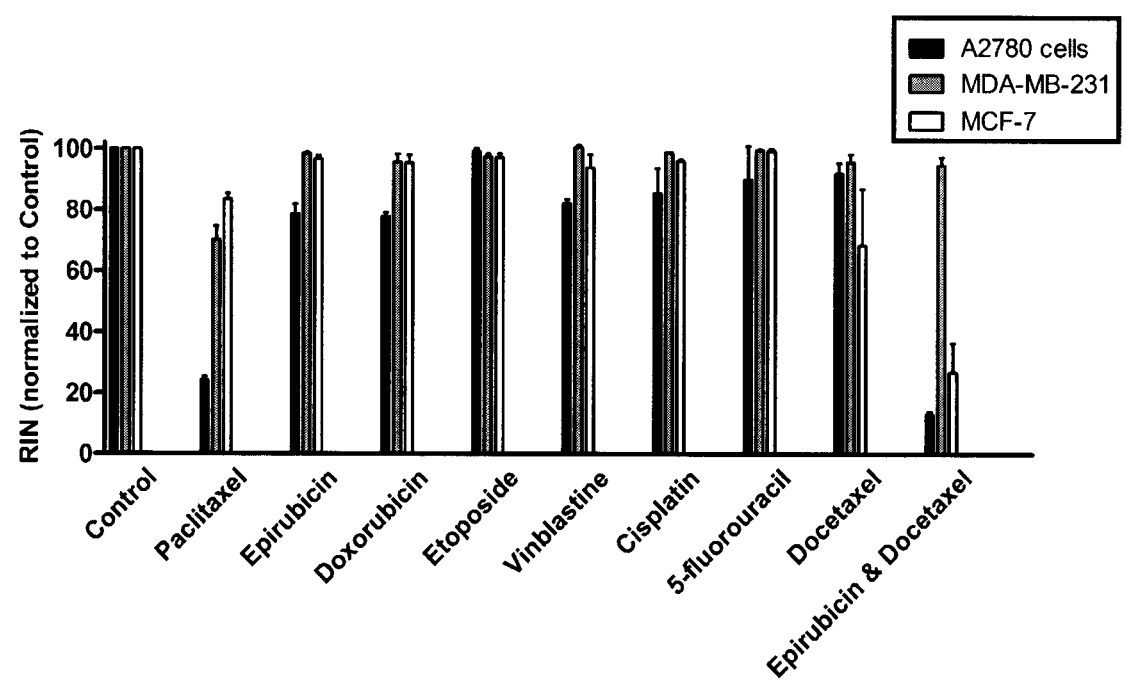
FIG. 4 is a graph showing the effect of various chemotherapy agents on cellular RIN.

Micromolar concentrations of the above drugs are, in many instances, above that typically used clinically, but the change in RNA integrity was measured over a 24 hour period, rather than over a period of 9 weeks (the time period that elapsed after initiation of treatment before tumour RNA integrity measurements were conducted in the MA.22 clinical trial). RNA integrity measurements in the cultured cells could not be extended well beyond 24 hours, because, even at lower drug concentrations, cells, in particular those with falling RNA integrity, detached from their tissue culture flasks and became nonviable shortly thereafter.

b) Effect of Epirubicin/Docetaxel on RNA Integrity in MCF-7 Breast Tumour Cells in Culture:

We then assessed whether a combination of epirubicin and docetaxel could induce strong reductions in RNA integrity (FIG. 2). Similar to our observations in the tumours of MA.22 patients, RNA integrity was dramatically reduced when to two agents were administered together (a mean drop in RIN of 78. % at 40 µM concentrations of each drug).

c) Synergistic Reductions in RIN by Co-Administration of Epirubicin and Docetaxel:

Using the above-described in vitro assay, it was then assessed within the same experiment whether epirubicin and docetaxel acted synergistically to induce greater reductions in RNA integrity than when the drugs were administered by themselves. As shown in FIG. 2, docetaxel only induced a modest 7.8% reduction in RNA integrity from 9.40±0.12 units to 8.67±0.42 units at the highest concentration of docetaxel (40 µM). Epirubicin at the same concentration was considerably better at inducing reductions in RNA integrity (37.7% reduction to 5.87±1.74 units. The combination of epirubicin and docetaxel (both at a 40 µM concentration) did indeed induce an even greater reduction (86.9%) in RNA integrity to 1.23±0.09 units. Taken together, our findings suggest that docetaxel induces minimal if any differences in RNA quality compared to epirubicin. A combination of the two drugs, however, produces more than an additive effect, indicating that docetaxel can synergize with epirubicin to substantially larger reductions in RNA integrity.

d) Ability of Other Drugs Classes to Induction Reductions in RNA Integrity in A2780 Cells:

The ability of a variety of drugs representing differences classes of chemotherapy agents to induce reductions in RNA integrity was then assessed. These included the topoisomerase II inhibitor etoposide, the vinca alkaloid vinblastine, the alkylating agent cisplatin, and the nucleoside analog 5-FI-uracil. A description of the distinct mechanisms of action of these various chemotherapy drugs can be found in our recent review [11]. Interestingly, the topoisomerase II inhibitor etoposide had no effect on RNA integrity in A2780 cells, not even at the highest concentration tested (40 µM). In contrast, doxorubicin, which also is a topoisomerase II inhibitor but has additional mechanisms of action, induced significant reductions in RNA integrity. This suggests that topoisomerase II inhibition does not contribute to the ability of doxorubicin to reduce cellular RIN. In contrast, vinblastine demonstrated a very clear ability to reduce RNA integrity (by almost two RIN units), even at the lowest concentration tested (2.5 µM). Significantly more loss or RNA integrity, however, was not observed when the drug concentration was increased up to and including 40 µM vinblastine. The DNA-damaging alkylating agent cisplatin exhibited the opposite effect on RNA integrity; low concentrations of cisplatin had no effect on RNA integrity. Only at the highest cisplatin concentration (40 µM) were substantial and statistically significant reductions in RIN values observed for A2780 cells. The nucleoside analog 5-FI-uracil also had no effect on RNA integrity until concentrations equalled or exceeded 20 µM.

e) Ability of Chemotherapy Agents to Induce Reductions in RNA Integrity in Addition Cell Lines of Varying Tissue Origins:

It was then assessed whether the above chemotherapy agents (at a 40 µM concentration) could induce changes in RNA integrity in a variety of cell lines of different tissue origins and whether these changes were consistent across the cell lines. As shown in FIG. 4, the ability of chemotherapy drugs to induce changes in RNA integrity varied significantly amongst the cell lines. For example, a large number of the representative chemotherapy agents were able to induce reductions in RNA integrity in A2780 ovarian cancer cells than any of the other cell lines assessed. Seven of the 8 chemotherapy drugs examined were able to reduce RNA integrity in A2780 cells at a 40 concentration . . . . Moreover, the studies were also able to provide evidence that a chemotherapy agent with a different mechanism of action (such as epirubicin) can synergize with taxanes to induce even greater reductions in RNA integrity.

Discussion

Cultured cell lines can often be highly useful in understanding the biology of disease. Breast cancer cell lines can strongly mimic the biological and genetic characteristics of primary tumours [12]. Moreover, it has been shown that breast cancer cell lines could be used to identify genetic and protein biomarkers whose expression can predict or indicate response to targeting therapies in breast cancer patients [13]. Interestingly, the findings described above indicate that, similar to the observations in tumours of locally advanced breast cancer patients in the MA.22 clinical trial, a combination of epirubicin and docetaxel can induce reductions in RNA quality (integrity) in MCF-7 breast tumour cell lines in vitro. Reductions in RNA integrity were dose-dependent, but required concentrations of these drugs that exceed that which could be safely administered to cancer patients. This may be because the drugs behave differently in patients than they do in cultured cells. For example, the drugs can have effects on tumour vascularization that would not be seen in our in vitro model. Secondly, RNA degradation was monitored after a brief period of incubation with the chemotherapy drugs (24 hours, as opposed to 9 weeks in the MA.22 clinical trial). In the experiments, cells could not be cultured for long time periods in the presence of chemotherapy drugs (even at significantly lower doses) without substantial loss of cell membrane integrity or cell viability. Nevertheless, it is interesting to note that it has been possible to establish in vitro models of chemotherapy-dependent RNA degradation.

Much can be learned from these in vitro models: For example, epirubicin and docetaxel (the two drugs used in the MA.22 clinical trial) can, by themselves, induce significant reductions in RNA integrity in A2780 cells. Moreover, this study documents a synergy between these two drugs, such that their combined effect on RNA integrity is greater than their individual effects. This synergy was necessary in order to see the effects of epirubicin in MCF-7 cells. There is clinical evidence that these two drugs act synergistically in the treatment of human ovarian tumours as well [14;15]. The studies in A2780 ovarian tumour cells also reveal that a wide variety of agents representing various classes of chemotherapy drugs can induce reductions in RNA integrity. These include another taxane (paclitaxel), another anthracycline (doxorubicin), the topoisomerase II inhibitor etoposide, the vinca alkaloid vinblastine, the alkylating agent cisplatin, and the nucleoside analog 5-FI-uracil. These findings indicate that reductions in tumour RNA integrity can be induced by a wide variety of chemotherapy agents. They further suggest that reductions in RNA integrity in vivo are likely not to be restricted to epirubicin and docetaxel.

Evidence provided herein, does, however, clearly indicate that some chemotherapy drugs appear to have greater capacity to reduce RNA quality. In A2780 cells, the drug etoposide (a topoisomerase II inhibitor) was unable to affect RNA integrity, even at the highest concentrations tested, suggesting that the drug may be unable to induce reductions in RNA integrity in vivo. Alternatively, since etoposide is only used to treat recurrent (drug-resistant) ovarian cancer [16;17], it is possible that etoposide would only show an ability to induce reductions in RNA integrity in ovarian tumours that have been selected for survival after primary chemotherapy. The dose-response curves for the various drugs that were able to affect RNA integrity were also quite distinct for each drug. For example, the anthracyclines epirubicin and doxorubicin and the vinca alkaloid vinblastine were all able to induce reductions in RNA integrity in A2780 cells at doses as low as 2.5 µM. As concentrations of these drugs were increased, RNA integrity fell proportionately, but eventually leveled off, such that further increases in drug dose were without effect. Docetaxel, in contrast, induced a minimal reduction in RNA quality, while paclitaxel induced the greatest reduction in RNA integrity by far, but only at concentrations equal to or exceeding 20 µM. Cisplatin and 5-fluorouracil induced more modest reductions in RNA integrity (again at concentrations ≥20 µM).

A large number of chemotherapy drug types (7 of 8) could induce a reduction in RNA integrity in A2780 cells. MDA-MB-231 cells resemble "triple negative" breast cancer, which lacks the Her-2, ER, and PR receptors and is much more difficult to treat with targeted and conventional chemotherapy regimens than ER positive, Her-2 negative breast cancer (representative of MCF-7 cells) [18]. In conclusion, the data presented in this study reveals that, similar to observations in the tumours of locally advanced breast cancer patients in the MA.22 clinical trial, MCF-7 breast tumour cell lines exposed to the same epirubicin/docetaxel combination in vitro also exhibited strong reductions in RNA integrity. Similar findings were observed for the drug combination in A2780 ovarian tumour cells. In A2780 cells, docetaxel and epirubicin, by themselves, could induce small reductions in RNA integrity, suggesting that the drugs, while synergistic, need not both be present to affect RNA integrity. The observation that 7 of 8 tested chemotherapy agents of varying structure could induce significant reductions in RNA integrity in A2780 ovarian tumour cells indicates that chemotherapy-dependent decreases in RNA integrity are not restricted to a select few types of chemotherapy agents.

Example 2

In vitro studies will be conducted to assess dose-dependent relationship between the RNA integrity value of ovarian tumour cells (after a 24 hours treatment with a specific chemotherapy drug or drug combination) and the number of colonies of >50 cells formed when the drug is removed and cells are introduced into a clonogenic assay. Colonies would be counted 7-10 days post introduction into the drug-free semi-solid medium used in the clonogenic assay.

Xenograft various ovarian tumour cells into nude mice to create ovarian tumours. Assess the ability of various drugs (alone or in combination) to induce reductions in tumour size and/or reductions in tumour RNA integrity as assessed using needle core biopsies and fine needle aspirates from the xenografted tumours. The effect of various regimens on survival post-treatment will also be assessed.

Survival will be assessed in animals whose tumours show dramatic reductions in RNA integrity during treatment and animals showing little change in RNA integrity.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

[1] A. Schroeder, O. Mueller, S. Stocker, R. Salowsky, M. Leiber, M. Gassmann, S. Lightfoot, W. Menzel, M. Granzow, and T. Ragg, The RIN: an RNA integrity number for assigning integrity values to RNA measurements, BMC. Mol. Biol. 7 (2006) 3.
[2] A. M. Parissenti, J. A. Chapman, H. J. Kahn, B. Guo, L. Han, P. O'Brien, M. P. Clemons, R. Jong, R. Dent, B. Fitzgerald, K. I. Pritchard, L. E. Shepherd, and M. E. Trudeau, Association of low tumor RNA integrity with response to chemotherapy in breast cancer patients, Breast Cancer Res. Treat. 119 (2010) 347-356.
[3] C. Cera, G. Palu, S. M. Magno, and M. Palumbo, Interaction between second generation anthracyclines and DNA in the nucleosomal structure, Nucleic Acids Res. 19 (1991) 2309-2314.
[4] S. Spadari, G. Pedrali-Noy, F. Focher, A. Montecucco, T. Bordoni, C. Geroni, F. C. Giuliani, G. Ventrella, F. Arcamone, and G. Ciarrocchi, DNA polymerases and DNA topoisomerases as targets for the development of anticancer drugs, Anticancer Res. 6 (1986) 935-940.
[5] N. R. Bachur, F. Yu, R. Johnson, R. Hickey, Y. Wu, and L. Malkas, Helicase inhibition by anthracycline anticancer agents, Mol. Pharmacol. 41 (1992) 993-998.
[6] R. Olinski, P. Jaruga, M. Foksinski, K. Bialkowski, and J. Tujakowski, Epirubicin-induced oxidative DNA damage and evidence for its repair in lymphocytes of cancer patients who are undergoing chemotherapy, Mol. Pharmacol. 52 (1997) 882-885.
[7] U. Vaishampayan, R. E. Parchment, B. R. Jasti, and M. Hussain, Taxanes: an overview of the pharmacokinetics and pharmacodynamics, Urology 54 (1999) 22-29.
[8] D. L. Morse, H. Gray, C. M. Payne, and R. J. Gillies, Docetaxel induces cell death through mitotic catastrophe in human breast cancer cells, Mol. Cancer Ther. 4 (2005) 1495-1504.
[9] T. Wieder, F. Essmann, A. Prokop, K. Schmelz, K. Schulze-Osthoff, R. Beyaert, B. Dorken, and P. T. Daniel, Activation of caspase-8 in drug-induced apoptosis of B-lymphoid cells is independent of CD95/Fas receptor-ligand interaction and occurs downstream of caspase-3, Blood 97 (2001) 1378-1387.
[10] W. G. McCluggage, Morphological subtypes of ovarian carcinoma: a review with emphasis on new developments and pathogenesis, Pathology 43 (2011) 420-432.
[11] A. M. Parissenti, S. L. Hembruff, D. J. Villeneuve, Z. Veitch, B. Guo, and J. Eng, Gene expression profiles as biomarkers for the prediction of chemotherapy drug response in human tumour cells, Anticancer Drugs 18 (2007) 499-523.

[12] J. Kao, K. Salari, M. Bocanegra, Y. L. Choi, L. Girard, J. Gandhi, K. A. Kwei, T. Hernandez-Boussard, P. Wang, A. F. Gazdar, J. D. Minna, and J. R. Pollack, Molecular profiling of breast cancer cell lines defines relevant tumor models and provides a resource for cancer gene discovery, PLoS. One. 4 (2009) e6146.

[13] R. M. Neve, K. Chin, J. Fridlyand, J. Yeh, F. L. Baehner, T. Fevr, L. Clark, N. Bayani, J. P. Coppe, F. Tong, T. Speed, P. T. Spellman, S. DeVries, A. Lapuk, N. J. Wang, W. L. Kuo, J. L. Stilwell, D. Pinkel, D. G. Albertson, F. M. Waldman, F. McCormick, R. B. Dickson, M. D. Johnson, M. Lippman, S. Ethier, A. Gazdar, and J. W. Gray, A collection of breast cancer cell lines for the study of functionally distinct cancer subtypes, Cancer Cell 10 (2006) 515-527.

[14] Bruckner, H W, Cagnoni, P J, Lee, J M, and et al. A sequence of adriamycin and Taxol infusions for refractory ovarian cancer. Proc. Am. Soc. Clin. Oncol. 13, 276. 1994. Ref Type Conference Proceeding

[15] V. J. O'Neill, S. B. Kaye, N. S. Reed, J. Paul, J. A. Davis, and P. A. Vasey, A dose-finding study of carboplatin-epirubicin-docetaxel in advanced epithelial ovarian cancer, Br. J. Cancer 86 (2002) 1385-1390.

[16] R. F. Ozols, Oral etoposide for the treatment of recurrent ovarian cancer, Drugs 58 Suppl 3 (1999) 43-49.

[17] T. Sugiyama, [Second-line chemotherapy for recurrent ovarian cancer], Gan To Kagaku Ryoho 32 (2005) 28-32.

[18] L. Carey, E. Winer, G. Viale, D. Cameron, and L. Gianni, Triple-negative breast cancer: disease entity or title of convenience?, Nat. Rev. Clin. Oncol. 7 (2010) 683-692.

The invention claimed is:

1. An in vitro method of identifying synergistic combinations of chemotherapeutic agents, comprising:
    a. harvesting human ovarian cancer cells, placing the harvested cells in different test wells, and incubating the harvested cells in the different test wells with each chemotherapeutic agent and with a combination of the chemotherapeutic agents for at least 1 hour;
    b. collecting floating and adherent ovarian cancer cells for each of the test wells;
    c. isolating RNA from each of the collected ovarian cancer cells to provide a RNA sample for each test well, said isolating comprising lysing the collected ovarian cancer cells in a RNA stabilizing composition, preparing a precipitation mixture of the lysed ovarian cancer cells, adding the precipitation mixture to a RNA isolating column and eluting the RNA from the column with a RNAse free liquid;
    d. determining a RNA integrity value of each RNA sample, said determining comprising separating the RNA sample using capillary electrophoresis apparatus; producing an electropherogram of the separated RNA sample and quantitating the RNA integrity of the separated RNA sample by assessing the electropherogram, wherein the RNA integrity value is a RNA integrity number (RIN);
    e. identifying the chemotherapeutic combination as synergistic when the reduction in RNA integrity is greater than any additive reduction in RNA integrity of the cancer cells treated with each agent of the combination alone or otherwise identifying the combination as non-synergistic; and
    f. testing the synergistic combinations in one or more assays selected from a clonogenic assay.

2. The method of claim 1, wherein the ovarian cancer cells are from an ovarian tumour sample obtained from a subject.

3. The method of claim 1, wherein the RNA integrity value indicative of synergy is decreased at least by 20%, at least 30%, at least 40%, at least 50%, at least 60%, at least 70%, at least 80% or at least 90% below an additive reduction.

4. The method of claim 1, wherein the RNA integrity value is determined by calculating a 28S:18S ribosomal (rRNA) ratio.

5. A method of treating a subject with ovarian cancer comprising:
    a. determining synergistic cancer responsiveness to a chemotherapeutic agent combination according to claim 1; and
    b. altering the cancer treatment to the combination, if the combination tested is synergistic.

6. The method of claim 1, wherein the combination of chemotherapeutic agents comprises an anthracycline and/or taxane.

7. The method according to claim 1, wherein the ovarian cancer cells are serous ovarian cancer cell line.

8. The method of claim 1, wherein the ovarian cancer cells are an A2780 cell line.

9. The method of claim 1, wherein the RNA integrity value is determined using an microcapillary electrophoresis machine.

10. The method of claim 6, wherein the taxane is selected from docetaxel, paclitaxel and combinations thereof.

11. The method of claim 6, wherein the anthracycline is selected from doxorubicin and epirubicin and combinations thereof.

12. The method of claim 1, wherein the ovarian cancer cells or the isolated RNA sample is sent to a testing site.

* * * * *